(12) United States Patent
Greenhalgh et al.

(10) Patent No.: US 10,500,030 B2
(45) Date of Patent: Dec. 10, 2019

(54) SURGICAL ATTACHMENT DEVICE

(71) Applicant: Tela Bio, Inc., Malvern, PA (US)

(72) Inventors: E. Skott Greenhalgh, Gladwyne, PA (US); John-Paul Romano, Chalfont, PA (US)

(73) Assignee: Tela Bio, Inc, Malvern, PA (US)

( * ) Notice: Subject to any disclaimer, the term of this patent is extended or adjusted under 35 U.S.C. 154(b) by 0 days.

(21) Appl. No.: 15/214,209

(22) Filed: Jul. 19, 2016

(65) Prior Publication Data

US 2016/0324618 A1 Nov. 10, 2016

Related U.S. Application Data

(62) Division of application No. 14/640,014, filed on Mar. 5, 2015, now Pat. No. 10,130,457.

(Continued)

(51) Int. Cl.
*A61F 2/00* (2006.01)
*A61F 2/12* (2006.01)
*A61L 31/00* (2006.01)
*A61L 31/14* (2006.01)
*A61L 27/24* (2006.01)

(52) U.S. Cl.
CPC .............. *A61F 2/0063* (2013.01); *A61F 2/12* (2013.01); *A61L 27/24* (2013.01); *A61L 31/005* (2013.01); *A61L 31/14* (2013.01); *A61F 2/0059* (2013.01); *A61F 2002/0068* (2013.01); *A61F 2210/0004* (2013.01); *A61F 2210/0076* (2013.01); *A61F 2220/0075* (2013.01); *A61F 2230/0008* (2013.01); *A61F 2240/001* (2013.01); *A61F 2250/003* (2013.01); *A61F 2250/0003* (2013.01); *A61F 2250/0017* (2013.01); *A61F 2250/0018* (2013.01); *A61F 2250/0023* (2013.01); *A61F 2250/0028* (2013.01); *A61F 2250/0029* (2013.01); *A61F 2250/0031* (2013.01); *A61F 2250/0078* (2013.01); *A61L 2430/04* (2013.01); *Y10T 29/49947* (2015.01)

(58) Field of Classification Search
CPC ........................................................ A61F 2/12
See application file for complete search history.

(56) References Cited

U.S. PATENT DOCUMENTS 5,593,441 A   1/1997   Lichtenstein et al.
5,919,232 A   7/1999   Chaffringeon et al.
(Continued)

FOREIGN PATENT DOCUMENTS

WO   WO 2003/082363   10/2003

OTHER PUBLICATIONS

Franklin, I.J. et al., "Uptake of Tetracycline by Aortic Aneurysm Wall and Its Effect on Inflammation and Proteolysis," *Brit. J. Surger*, 86(6):771-775, 1999.

(Continued)

*Primary Examiner* — Suba Ganesan
*Assistant Examiner* — Aren Patel
(74) *Attorney, Agent, or Firm* — Levine Bagade Han LLP

(57) ABSTRACT

A hybrid medical device that can aid in reconstructive or augmentative surgery of the breast is disclosed. The device can utilize a suitable biological collagen tissue matrix combined with a synthetic material, for example, that can impart a high initial strength to the repair site while permitting proper healing and revitalization of the implanted device.

20 Claims, 9 Drawing Sheets

Related U.S. Application Data

(60) Provisional application No. 61/948,518, filed on Mar. 5, 2014.

(56) References Cited

U.S. PATENT DOCUMENTS

| | | | |
|---|---|---|---|
| 9,775,700 B2 | 10/2017 | Greenhalgh et al. | |
| 10,130,457 B2 | 11/2018 | Greenhalgh et al. | |
| 2003/0023316 A1 | 1/2003 | Brown et al. | |
| 2003/0225355 A1 | 12/2003 | Butler | |
| 2004/0138762 A1 | 7/2004 | Therin et al. | |
| 2004/0249457 A1* | 12/2004 | Smith | A61F 2/12 623/7 |
| 2005/0070930 A1 | 3/2005 | Kammerer | |
| 2005/0113849 A1 | 5/2005 | Popadiuk et al. | |
| 2005/0113938 A1 | 5/2005 | Jamiolkowski et al. | |
| 2007/0088434 A1* | 4/2007 | Frank | A61F 2/12 623/8 |
| 2008/0086216 A1 | 4/2008 | Wilson et al. | |
| 2008/0097601 A1* | 4/2008 | Codori-Hurff | A61F 2/12 623/8 |
| 2009/0018655 A1 | 1/2009 | Brunelle et al. | |
| 2009/0082864 A1* | 3/2009 | Chen | A61F 2/12 623/8 |
| 2009/0216338 A1 | 8/2009 | Gingras et al. | |
| 2010/0063599 A1 | 3/2010 | Brunelle et al. | |
| 2010/0217388 A1* | 8/2010 | Cohen | A61F 2/0059 623/8 |
| 2010/0318124 A1 | 12/2010 | Leung et al. | |
| 2011/0125287 A1* | 5/2011 | Hotter | A61B 17/06166 623/23.72 |
| 2011/0166673 A1 | 7/2011 | Patel et al. | |
| 2011/0257761 A1 | 10/2011 | Mortarino | |
| 2011/0301717 A1 | 12/2011 | Becker | |
| 2012/0010637 A1 | 1/2012 | Stopek et al. | |
| 2012/0082712 A1 | 4/2012 | Stopek et al. | |
| 2012/0095482 A1 | 4/2012 | Peterson et al. | |
| 2012/0143329 A1 | 6/2012 | Kim | |
| 2012/0165957 A1 | 6/2012 | Everland et al. | |
| 2012/0179176 A1 | 7/2012 | Wilson et al. | |
| 2012/0184974 A1 | 7/2012 | Becker | |
| 2013/0172994 A1 | 7/2013 | Becker | |
| 2013/0317286 A1 | 11/2013 | Bluecher et al. | |
| 2014/0142520 A1 | 5/2014 | Stopek et al. | |
| 2015/0112434 A1* | 4/2015 | Felix | A61L 31/148 623/8 |
| 2015/0127103 A1 | 5/2015 | Seedhom | |
| 2015/0250582 A1 | 9/2015 | Greenhalgh et al. | |
| 2015/0297798 A1 | 10/2015 | Badylak et al. | |
| 2017/0020648 A1 | 1/2017 | Greenhalgh et al. | |
| 2017/0027678 A1 | 2/2017 | Greenhalgh et al. | |
| 2017/0245847 A1 | 8/2017 | Obermiller et al. | |
| 2019/0008623 A1 | 1/2019 | Nemoto et al. | |

OTHER PUBLICATIONS

Pyo, R. et al., "Targeted Gene Disruption of Matrix Metalloproteinase-9 (Gelatinase B) Suppresses Development of Experimental Abdominal Aortic Aneurysms," *J. Clinical Investigation*, 105(11):1641-1649, Jun. 2000.

Tambiah, J. et al., "Provocation of Experimental Aortic Inflammation Mediators and Chlamydia Pneumoniae," *Brit., J. Surgery*, 88(7):935-940, Feb. 2001.

Walton, L.J. et al., "Inhibition of Prostoglandin E2 Synthesis in Abdonminal Aortic Aneurysms," *Circulation*, 48-54, Jul. 6, 1999.

Xu, Q. et al., "Sp1 Increases Expression of Cyclooxygenase-2 in Hypoxic Vascular Endothelium," *J. Biological Chemistry*, 275(32):24583-24589, Aug. 2000.

* cited by examiner

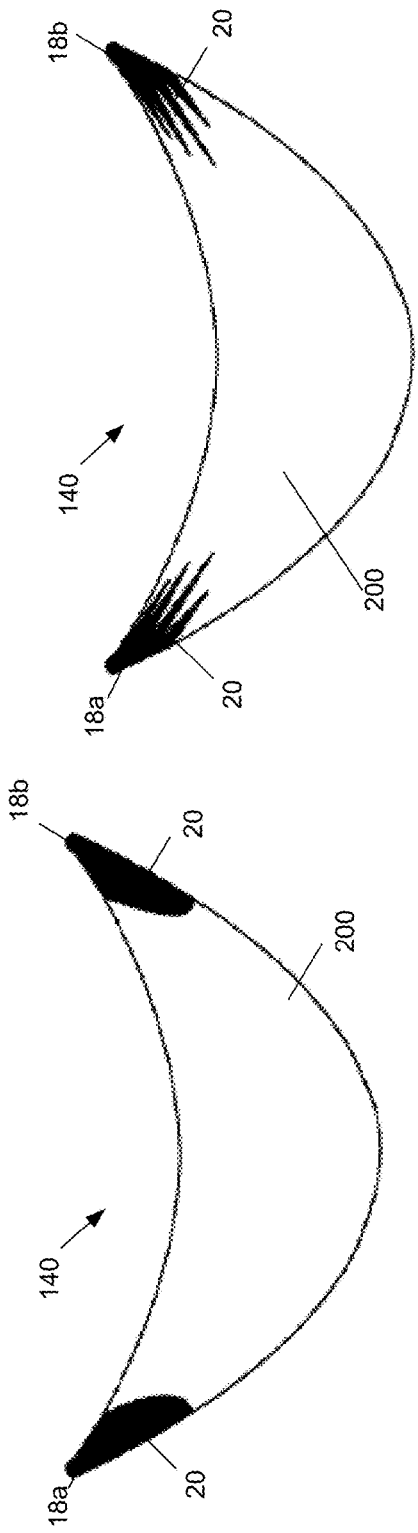
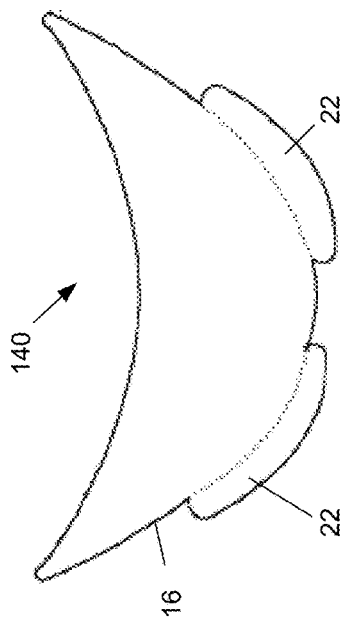
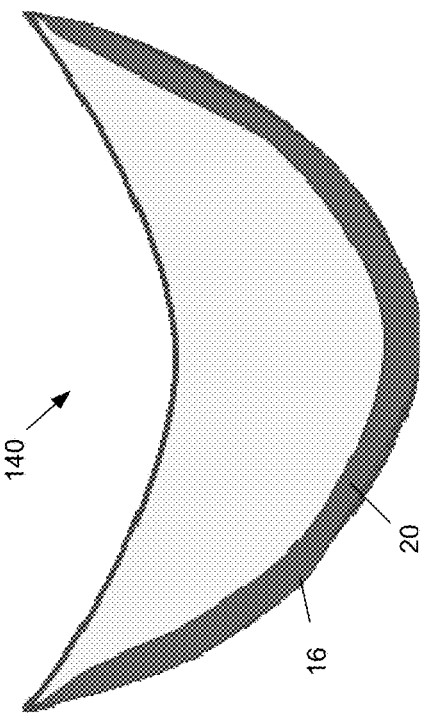

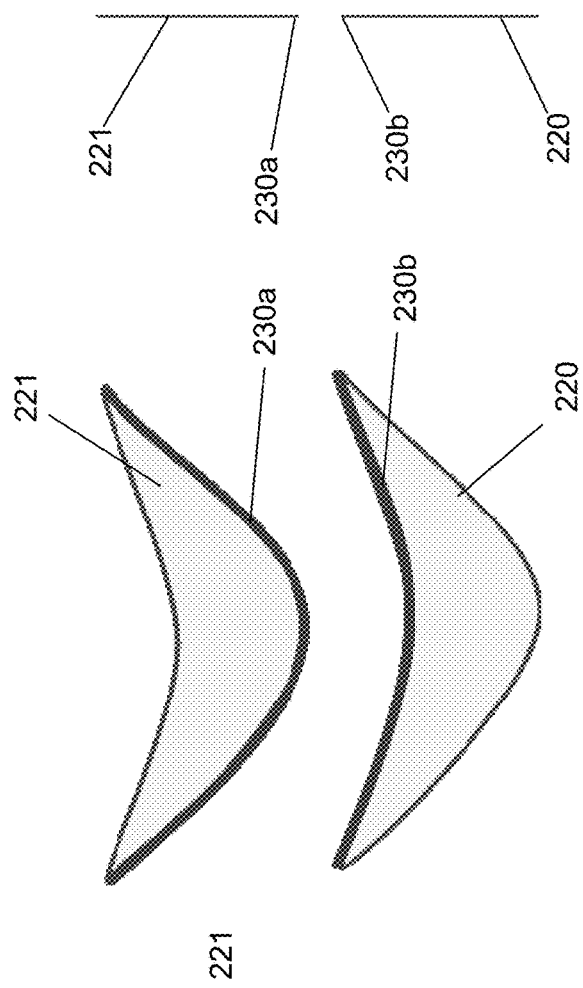
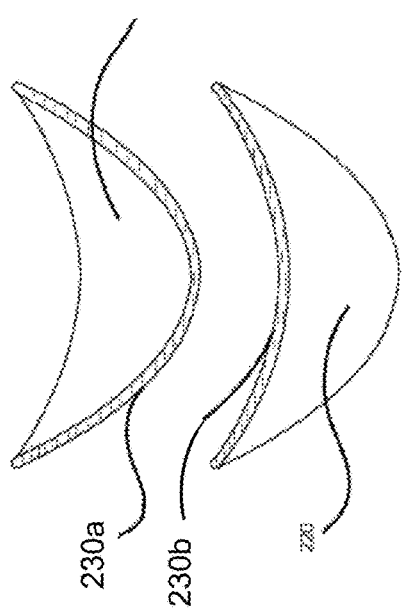
Fig. 17a  Fig. 17b  Fig. 17c

SURGICAL ATTACHMENT DEVICE

CROSS-REFERENCE TO RELATED APPLICATION

The present application is a divisional application of U.S. patent application Ser. No. 14/640,014, filed Mar. 5, 2015, which claims the benefit of U.S. Provisional Application No. 61/948,518, filed Mar. 5, 2014, both of which are incorporated by reference herein in their entireties.

BACKGROUND

1. Technical Field

The present disclosure relates to implantable repair matrices and more particularly to combination matrices wherein the implantable material can have a biologic matrix and an integrated supporting synthetic matrix.

2. Description of the Related Art

Breast reconstruction surgery (BRS) encompasses several techniques for reproducing the shape and size of a breast that has been lost because of a mastectomy. Often these endpoints are unpredictable, as a surgeon cannot predict with 100% confidence how a reconstructed breast will heal.

Generally, while BRS may be performed at the same time as the mastectomy, or delayed for sometime after the initial removal surgery, pockets are formed under the pectoralis muscles in preparation for implant placement. When the pockets are formed for the implants, a patient's tissue typically requires expansion or stretching.

Certain complications may present during healing of a reconstructed breast. Among these are infection, pain, contraction and/or implant migration. It has been shown that placement of a biologic support in conjunction with a separate implant may help alleviate many or all of these complications. However, these biologic supports are limited in their ability to control and shape physical properties of the implant.

There is a need for devices which support natural breast tissue or implant devices and which allow greater control of surgical positioning of implants, post-operative healing of the reconstruction site as well as long term health and appearance of the reconstructed breast.

SUMMARY OF THE INVENTION

A surgical attachment device, such as a hybrid implantable breast reconstruction/augmentation device for maximal control and support of an associated breast implant while minimizing healing time and post-operative complications, is disclosed. The hybrid device can have a processed biologic sheet or scaffold that can have a synthetic material. The synthetic material can be in the form of threads, webs, sheets or combinations thereof. The device may have single or multiple layers of scaffold. The device may contain integrated synthetic biodegradable or nonbiodegradable polymer material for the reconstructive procedure.

The biologic component may have one or more layers of a biologic material that are capable of remodeling and/or revitalizing so as to integrate with the host. For example, allogeneic or xenogeneic materials such as collagen sheets, dermal matrices, organ matrices, epithelial substrata matrices such as bladder; pericardium; intestinal submucosal layers; stomach; forestomach or other digestive tract submucosa; stomach; forestomach sub-epithelial collagenous layers or other epithelial or endothelial sub-strata layers.

The device may have combinations of biological scaffold layers intermingled with layers of synthetic material. Such synthetic material layers may be comprised of non-degrading biomaterials such as PET, Polypropylene, PTFE ePTFE; or biodregrading materials such as PGA; PLA; PLLA; peL; nylon, silk or collagen based materials.

The layers may have been bonded at certain areas by tissue welds, biological or surgical adhesives or suture type materials in order to facilitate the optimal surgical placement and integration of the device.

The device may have a polymer or bonding reinforcement of tissue or tissue/synthetic polymer combination in a highly controlled manner. For example, bonding or suture patterns may create an anisotropic membrane; polymer or bonding rich sites to create seams for complex three-dimensional shaping (for example cupping, tabs, pockets, curves); engineering the polymer or bonding sites to provide localized suture reinforced zones as in tissue-to-muscle-wall attachment; using the properties of polymer or bonding sites to change the tissue's ability to heal or scar as in, for example, anchoring implants and device in place to prevent or minimize migration of the implant; the use of integrated tethers to aid in placement as in minimally invasive implantation techniques.

The suture or thread material can have a variable diameter, material type, monofilament or braided multi-filament and/or resorbable vs. non-resorbable. The device can have focal areas of increased suture density; increased number of tissue layers or multi-layer bonds may provide attachment points suitable for external suture application, modulate healing response, encourage endogenous tissue formation, promote or modulate adhesions or other mechanisms which are designed to secure the matrix to the implant site or control the healing response.

Individual layers of a multi-layer device may be constructed so that the densest suture patterns are confined to the inner layer or layers with the outer layers minimally sutured or otherwise anchored in place. Upon implantation, the minimally attached, penetrated or otherwise compromised outer layers of the device serve to minimize the potential for abrasion, inflammation and/or adhesion formation when in contact with surrounding tissue. Layers of synthetic biodegradable or non-biodegradable material may be interleaved with layers of biological material to provide, for example, maintenance of shape, increased strength, release of bioactive compounds, maintenance of shape during remodeling or to provide reservoirs for cells or bioactive products.

The device can have structured gradients in material properties of the device. For example, gradients in strength, elongation or thickness, for example, by variations in density of suture or thread penetrations; the integration of suture or thread patterns or designs into the device or the inclusion of varied numbers of layers of biologic or synthetic material within a hybrid construct so as to provide localized areas of increased or decreased layer number.

The multiple layers of biologic material or defined areas of the biologic layer material may be held in approximation to other layers via mechanisms such as, glues or adhesives, tissue welding, or combinations thereof.

The glues or adhesives can be organic, natural or synthetic. The adhesives may comprise bio-compatible "super glue" type cyanoacrylate or methacrylates, bio-type glues such as fibrin/thrombin, light-activated adhesive materials, or combinations thereof.

The tissue welding techniques can be thermal, ultrasound, RF or IR energy patterns, the use of other wavelengths of electromagnetic energy such as laser type concentrated energy sources, or combinations thereof.

The device can have various holes, apertures, slits, pores or other fluid transport and/or control features, or combinations thereof. A slit can be a cut without material removal into a single or multiple layers of the device. The slits may be uni-directional (i.e existing along one axis of the device) or multi-directional. The fluid transport and/or control features can manage fluid transport within or through the implanted matrix construct as in, for example prevention of postoperative seroma formation. These transport or control features may be aligned or offset through adjacent layers of a multi-layer construct device and could, for example, be produced via die cutting, water jet, laser or combinations thereof.

BRIEF DESCRIPTION OF THE DRAWINGS

FIGS. 1 through 11 illustrate variations of the device.

FIGS. 17a through 17c are variations of perspective, front, and side views of components of the device during manufacturing.

DETAILED DESCRIPTION

Figure 1:
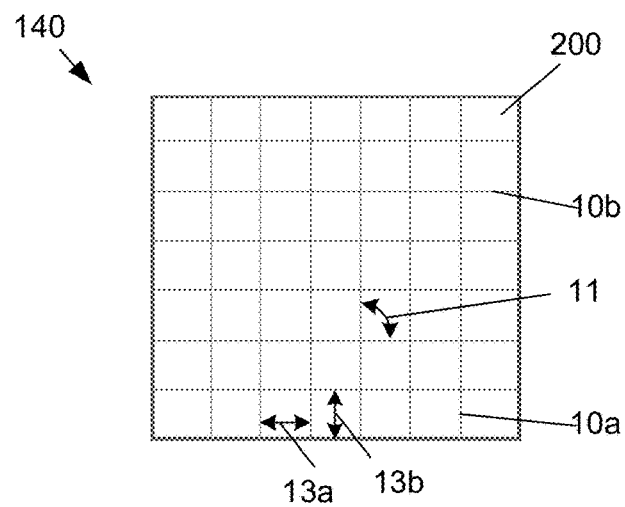

FIG. 1 illustrates that a surgical attachment device 140, such as a reinforcement or bridging patch, can be made from a biologic sheet, backing, matrix, or scaffold 200, and one or more synthetic or other exogenous reinforcing longitude or longitudinal (or radial) leaders 10a and/or lateral or latitudinal (or angular) leaders 10b, such as polymer sutures, attached to the scaffold 200. The leaders 10 can be inside and/or outside the material of the scaffold 200. The device 140 can deliver a structural (e.g., biomechanical) supporting force to surrounding tissue and/or implants.

The scaffold 200 can a collagen sheet with cells removed or otherwise made animal tissue, such as an extracellular matrix (ECM) derived from the forestomach of a ruminant, such as a sheep. Exemplary scaffolds are described in U.S. Pat. No. 8,415,159, which is incorporated by reference herein in its entirety. The scaffold 200 can have about 70% or more, more narrowly about 80% or more, for example 100% of the cells, or from about 70% to about 80% of the cells removed or disrupted to remove the antigenic component of the disrupted cells.

The scaffold 200 can be made from one of more (e.g., two, four, six, or eight) layers of extracellular matrix. The scaffold and/or individual layers can have a thickness from about 1 mm to about 4 mm, for example about 1.8 mm. The scaffold and/or individual layers can also have a thickness from about 0.1 mm to about 0.2 mm. The layers can be bonded together. Bonding may be accomplished by the use of biodegradable or non-biodegradable suture type materials, such as stitching by the leaders 10, by tissue welding via RF frequency energy, biologic-type glues such as cyanoacrylate derivatives, fibrin/thrombin; gelatins, gluteraldehydes; or other artificial polymers or combinations thereof. The bonded areas may exist as discrete islands or as a single or multiple strips or areas of increased polymer or bonding content.

The longitudinal leaders 10a can intersect the latitudinal leaders 10b at intersection angles 11. The intersection angles 11 can be from about 5° to about 175°, more narrowly from about 45° to about 135°, for example about 90°. The longitudinal leaders 10a can be parallel or non-parallel with each other. The latitudinal leaders 10b can be parallel or non-parallel with each other.

The leaders 10 can be stitched into or through the scaffold 200. The stitching can have stitch patterns with stitch lengths from about 1 mm to about 3 mm, for example about 1.5 mm.

Figure 5:
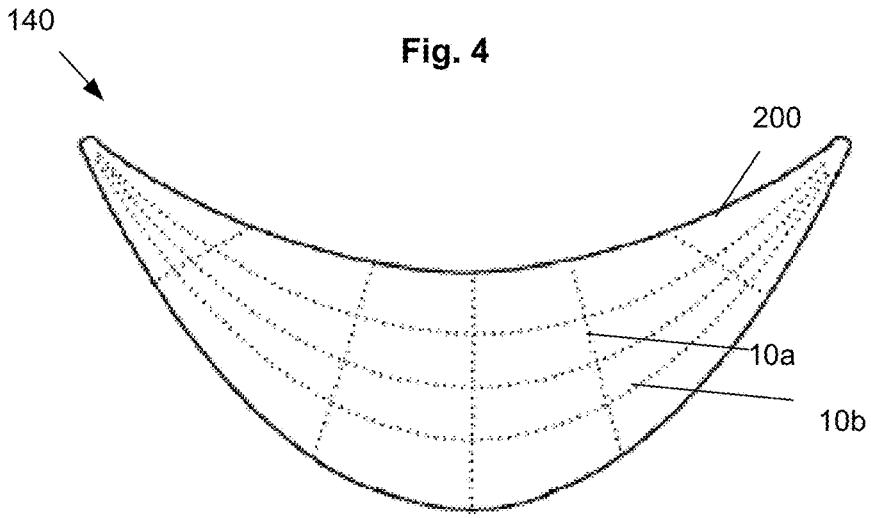

The longitudinal leaders 10a can be spaced apart by a longitudinal leader gap 13a from about 1 mm to about 25 mm, more narrowly from about 1 mm to about 12 mm, for example about 6 mm. The longitudinal leaders 10a can be spaced apart by a longitudinal leader gap 13a from about 1 mm to about 25 mm, more narrowly from about 1 mm to about 12 mm, for example about 6 mm. The leader gaps 13 can remain constant (as shown in FIG. 1) or vary (as shown in FIG. 5) across the length and/or width of the device 140.

The leaders 10 can be made from any of the materials disclosed herein or combinations thereof, such as a non-biodegrading polymer, such as polypropylene, ultra-high-molecular-weight polyethylene (UHMWPE), PET, PTFE, ePTFE, or combinations thereof. The leaders 10 can be monofilaments or multifilaments. The leaders 10 and/or the filaments can have diameters from about 0.002 in. to about 0.02 in., more narrowly from about 0.002 in. to about 0.01 in., yet more narrowly from about 0.006 in. to about 0.008 in., for example about 0.008 in.

The longitudinal leaders 10a can extend across 90% or more, for example across the entire length, of the scaffold 200 and/or device 140, for example extending from the bottom (as seen in the figure relative to the page) terminal edge to the top terminal edge. The lateral leaders 10b can extend across 90% or more, for example across the entire length, of the scaffold 200 and/or device 140, for example extending from the left (as seen in the figure relative to the page) terminal edge to the right terminal edge.

The device 140 can have a square or rectangular shape.

Figure 2:
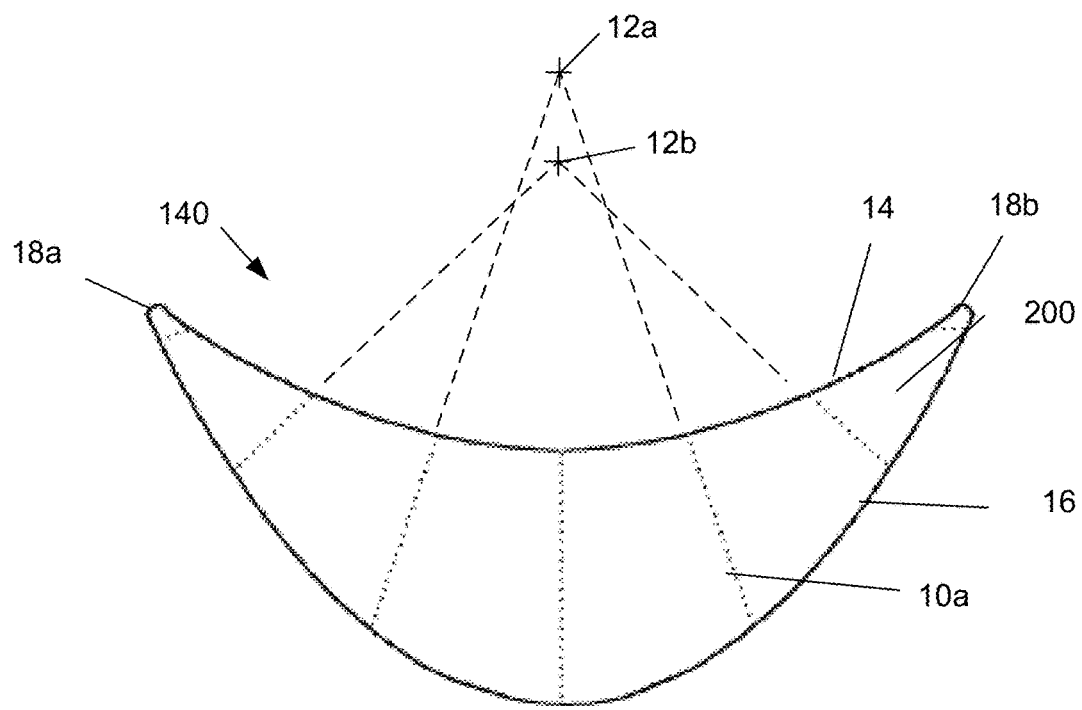

FIG. 2 illustrates that the device 140 can have a crescent shape. The crescent shape can have a left corner point or tip 18a and a right corner point or tip 18b. The device 140 can have a curved, convex distal edge 14 (for attachment to a soft tissue, such as muscle away from the center of the body) and a curved, concave proximal edge 16 (for attachment to a bone and/or soft tissue, such as fascia or muscle closer to the center of the body than the distal edge 14).

The device 140 can have longitudinal leaders 10a, but no lateral leaders 10b. The longitudinal leaders 10a can extend from the distal edge 14 to the proximal edge 16.

The longitudinal leaders 10b can radially extend from a common radial axis 12. For example, all of the longitudinal leaders can radially extend from the same axis, or laterally symmetric pairs of longitudinal leaders 10b can extend from common radial axes, such as the first radial axis 12a and the second radial axis 12b. The radial axis or axes 12 can be located not on or extending through the device 140. The radial axis or axes 12 can be located distal of the distal edge 14 (i.e., with the longitudinal leaders 10a extending apart from each other as they approach the proximal edge 16) or proximal of the proximal edge 16 (i.e., with the longitudinal leaders 10a extending apart from each other as they approach the distal edge 14). The longitudinal leaders 10a can extend in substantially straight (as shown) or curved directions, as viewed from above or below the device 140.

Figure 3:
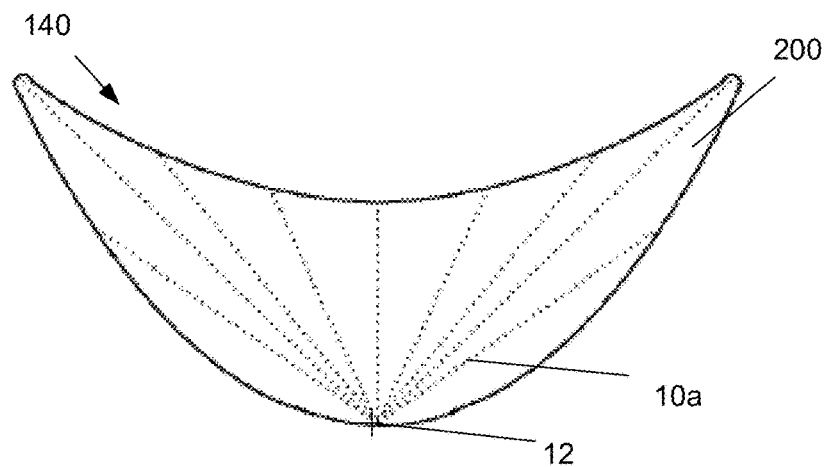

FIG. 3 illustrates that the radial axis 12 can be located on and/or extend through the device 140. The radial axis 12 can be located closer to the proximal edge 16 (as shown) distal edge 14, or evenly between the two edges 14 and 16. The radial axis 12 can be located laterally centered (as shown) to the device 14 or laterally off-center to the device 14.

Figure 4:
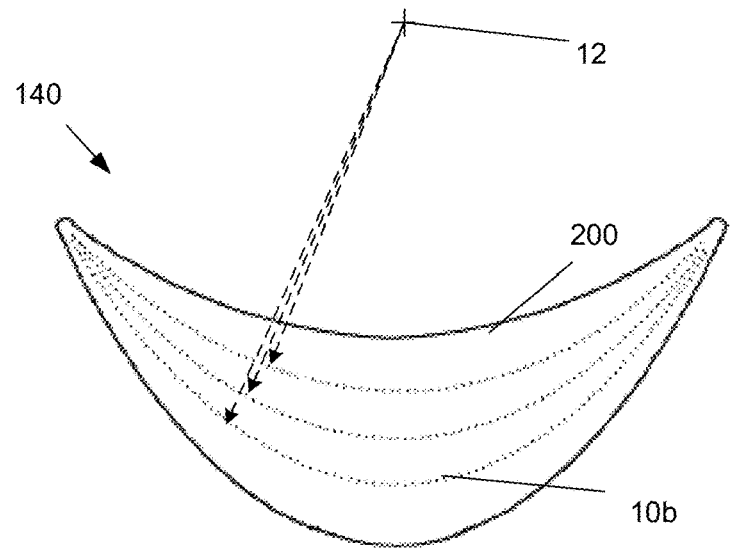

FIG. 4 illustrates that the device 140 can have latitudinal leaders 10b, but no longitudinal leaders 10b. The latitudinal leaders 10b can extend around a common radial axis 12 along the entire length of the latitudinal leaders or at a given radius extending through the latitudinal leaders 10b. The latitudinal leaders 10b can extend in substantially straight or curved (oval, as shown, but also can be circular), as viewed from above or below the device 140.

FIG. 5 illustrates that the crescent-shaped device 140 can have longitudinal and latitudinal leaders 10a and 10b. The device 140 can have the same or differing densities and/or quantities of longitudinal leaders 10a compared to lateral leaders 10b.

Figure 6:
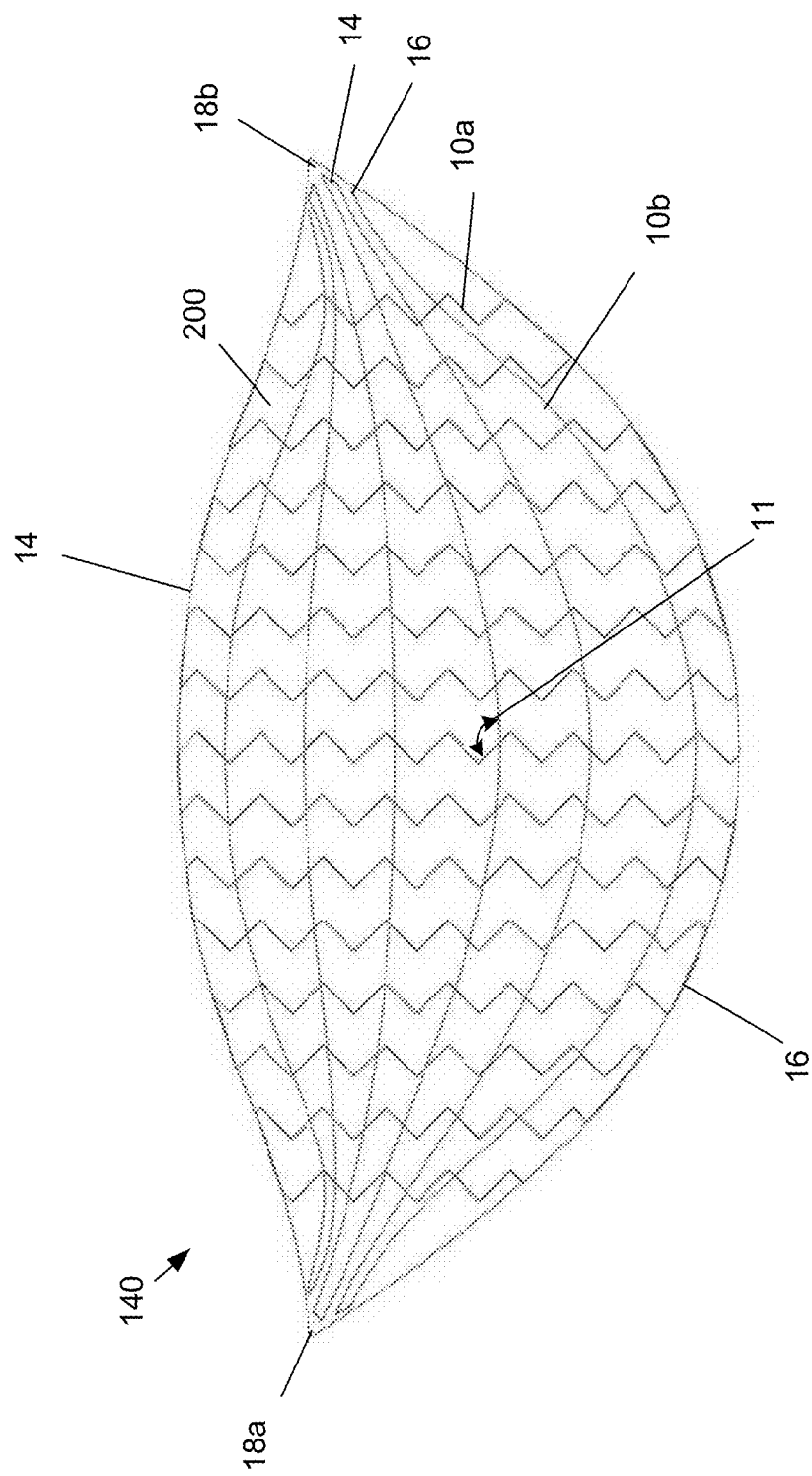

FIG. 6 illustrates that the distal edge 14 can be convex.

The longitudinal leaders 10a (as shown) and/or latitudinal leaders 10b can have sinusoidal and/or zig-zag (e.g., Z-shaped, W-shaped, and V-shaped), as shown, stitching patterns. The leaders 10 can form right angles in the stitching patterns. The longitudinal leaders 10b can be longer in the lateral center of the device 140 and shorter toward each of the lateral sides of the device 140.

Longitudinal leaders 10a and/or latitudinal leaders 10b can terminate at the edges 14 and 16 or tips 18 (as shown for the longitudinal leaders 10a), and/or terminate before the edges 14 and 16 or tips 18, and/or can return to traverse the scaffold 200 without terminating at the edges 14 and 16 or tips 18 (as shown for the latitudinal leaders 10b).

FIG. 7 illustrates that the device 140 can have reinforced anchors 20 at the tips 18. The anchors 20 can be or have a higher concentration of polymer and/or thicker scaffolding (e.g., with more or thicker layers than the remainder of the device 140). For example, the anchors 20 can be or have polymer caps. The anchors 20 can be a significantly higher density (e.g., more than three times) of leaders 10 than the density of leaders 10 in the remainder of the device 140. The anchors can be formed by increasing the relative percent bonding content, by increasing the amount or layers of scaffold tissue matrix material, or combinations thereof. The anchors 20 can be over or embedded in the scaffold 200. The anchors 20 can have smooth edges.

During use, the device 140 can be inserted to the target site and attached to the target site solely with attachment elements, such as hooks, brads, staples, sutures, or combinations thereof, through the anchors 20.

FIG. 8 illustrates that the anchors 20 can have irregular-shaped edges. For example, the edge of the anchors 20 attaching to the scaffold 200 can be pointed or spiky. The anchoring force load can be passively distributed across the edge of the anchor 20 to the scaffold 200.

FIG. 9 illustrates that the anchor 20 can extend from left tip 18a to the right tip 18b along the proximal edge 16 (as shown) and/or the distal edge 14. The anchor 20 can extend partially along one or both edges 14 and 16 without extending to one or both tips 18.

The anchors 20 can provide points for surgical attachment, provide areas of increased strength or thickness where increased stress is expected post operatively, aid in producing a post-surgical shape of the device 140, or combinations thereof.

FIG. 10 illustrates that the device 140 can have one or more extension flaps or fillers 22 extending proximally from the proximal edge 16 (as shown) and/or distal edge 14. The fillers 22 can be laterally symmetric (as shown) or asymmetric. The fillers 22 can be square, rectangular, circular, oval, or cut-off portions of those shapes. The fillers 22 can be extensions of the scaffold 200 or different material than the scaffold 200. The fillers 22 can have the same, a thinner, or a thicker thickness than the scaffold 200.

Figure 11:
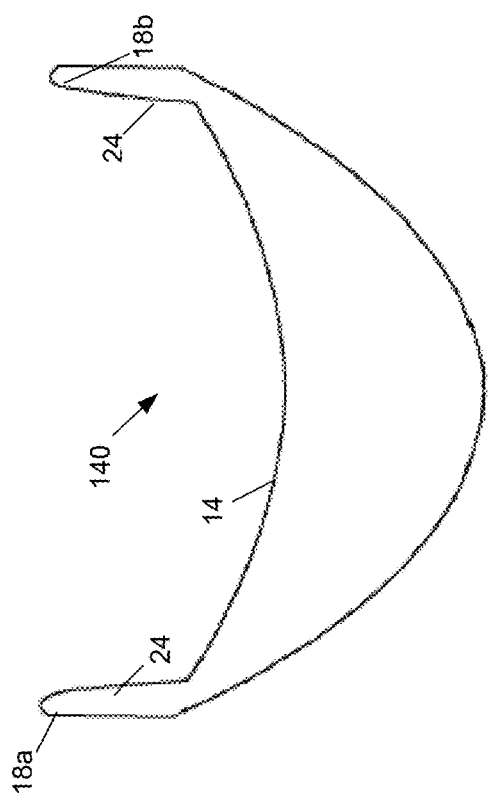

FIG. 11 illustrates that the device can have tabs, tethers, or tip extenders 24 extending in a distal direction from the distal edge 14. The extenders 24 can be laterally symmetric (as shown) or asymmetric. The extenders 24 can be extensions of the scaffold 200 or different material than the scaffold 200. The extenders 24 can have the same, a thinner, or a thicker thickness than the scaffold 200.

The fillers 22 and/or extenders 24 can be used for surgical attachment and/or manipulation.

Figure 12A:
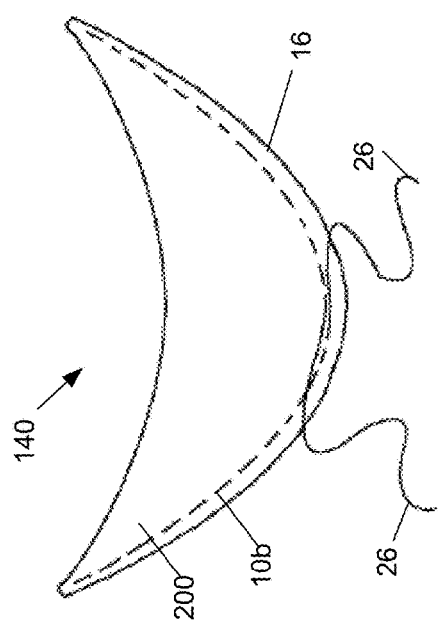
FIGS. 12a through 12c illustrate a variation of the device and a method for using the same.

FIG. 12a illustrates that one or more of the leaders 10 (the proximal-most latitudinal leader 10b is shown) can have both of its leader terminal ends 26 that can be loose and extend out of the scaffold 200, for example in the direction of the distal edge 14 or proximal edge 16 (as shown). The leader terminal ends 26 can be pulled to tension the respective leader and cinch the device 140 (e.g., a "purse string" or "shoe string" effect).

Figure 12C:
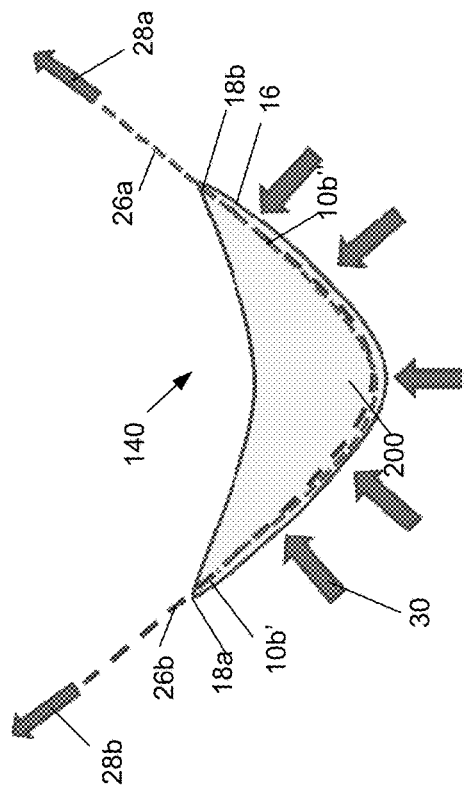
Figure 12B:
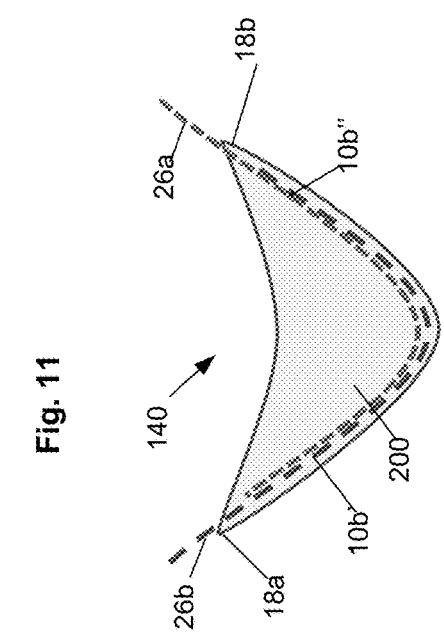

FIG. 12b illustrates that a first latitudinal leader 10b' can have a first leader terminal end 26a that can extend out of the scaffold 200 at the right tip 18b, and a second terminal end that can terminate in the scaffold 200. A second latitudinal leader 10b" can have a second leader terminal end 26b that can extend out of the scaffold 200 at the left tip 18a, and a second terminal end that can terminate in the scaffold 200. The first latitudinal leader 10b' can be the adjacent latitudinal leader to the second latitudinal leader 10b".

FIG. 12c illustrates that a first tensioning force, shown by arrow 28a, can be applied to the first leader terminal end 26a in the terminal direction of the first leader terminal end 26a. A second tensioning force, shown by arrow 28b, can be applied to the second leader terminal end 26b in the terminal direction of the second leader terminal end 26b. The tensioning forces 28 can cause the first and second latitudinal leaders 10b' and 10b" to deliver a cinching force, shown by arrows 30, to the scaffold 200 adjacent to the respective leaders 10b' and 10b".

Figure 13:
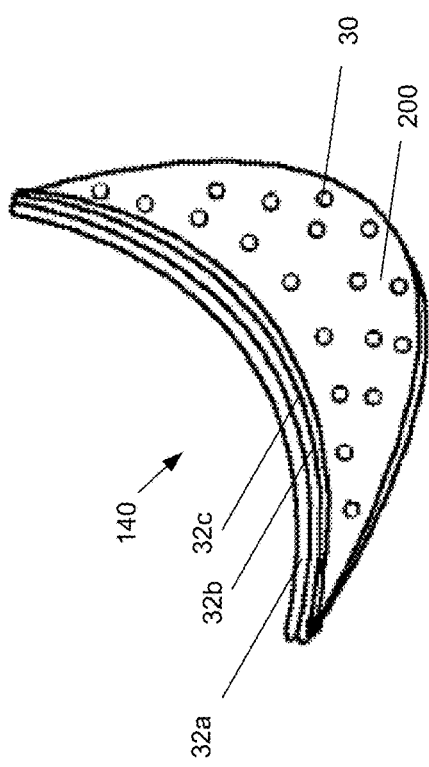
FIG. 13 illustrates a variation of the device.

FIG. 13 illustrates that the device 140 and/or scaffold 200 can have round (as shown) or square pores 30 with pore diameters or widths from about from about 1 mm to about 12 mm, for example about 6 mm.

One or more of the scaffold's layers 32, such as an inner layer 32a, middle layer 32b, and outer layer 32c, can have pores 30. The pores 30 can completely or partially align (i.e., be congruent) between the layers 30, for example creating an open channel and allowing fluid communication between the external sides or faces of the scaffold 200. The pores 30 can be offset between the layers 32 forming a tortuous or incomplete path between the external sides or faces of the scaffold 200.

Tissue ingrowth (i.e., repopulation) can pass through the pores 30. Biological or other fluids can pass through the pores 30. For example, drainage through the pores 30 can decrease seroma formation. The pores 30 can be slits (e.g., wherein no material has been removed), and/or holes (e.g., created by the removal of material).

Figure 14C:
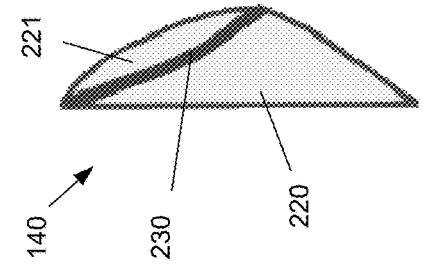
FIGS. 14a through 14c are perspective, bottom, and side views, respectively, of a variation of the device.
Figure 14B:
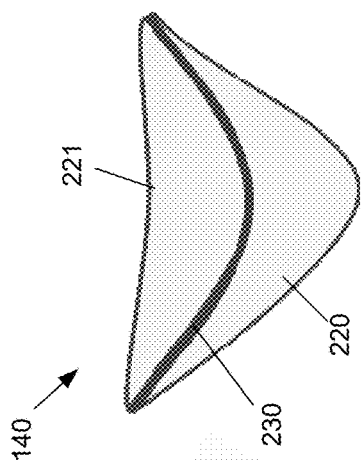
Figure 14A:
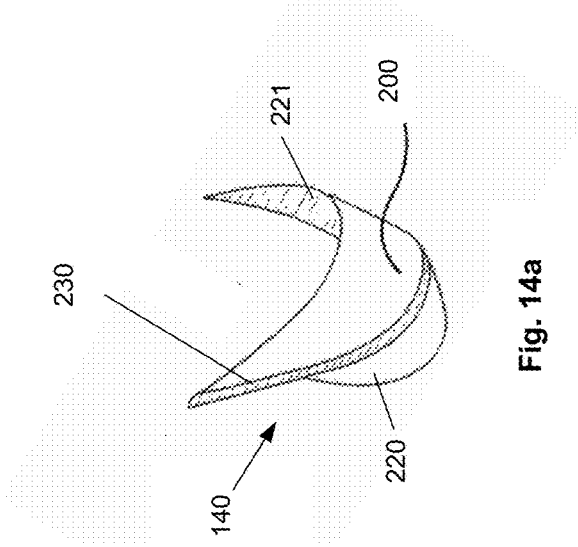

FIGS. 14a through 14c illustrate that the scaffold 200 can have a scaffold first panel 220 and a scaffold second panel 221. The scaffold first and second panels 220 and 221 can be bonded to each other along a seam or margin 230. The device 140 can have a cupped or bowled shape with a cavity.

Any or all elements of the device 140 and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CON-ICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphthalate (PET), polyester (e.g., DACRON® from E. I. Du Pont de Nemours and Company, Wilmington, Del.), poly ester amide (PEA), polypropylene, aromatic polyesters, such as liquid crystal polymers (e.g., Vectran, from Kuraray Co., Ltd., Tokyo, Japan), ultra-high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

The device 140 can be made from substantially 100% PEEK, substantially 100% titanium or titanium alloy, or combinations thereof.

Any or all elements of the device 140 and/or other devices or apparatuses described herein, can be, have, and/or be completely or partially coated with agents for cell ingrowth.

The device 140 and/or elements of the device and/or other devices or apparatuses described herein can be filled, coated, layered and/or otherwise made with and/or from cements, fillers, and/or glues known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rh-BMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, Circulation, Jul. 6, 1999, 48-54; Tambiah et al, Provocation of Experimental Aortic Inflammation Mediators and Chlamydia Pneumoniae, Brit. J. Surgery 88 (7), 935-940; Franklin et al, Uptake of Tetracycline by Aortic Aneurysm Wall and Its Effect on Inflammation and Proteolysis, Brit. J. Surgery 86 (6), 771-775; Xu et al, Sp1 Increases Expression of Cyclooxygenase-2 in Hypoxic Vascular Endothelium, J. Biological Chemistry 275 (32) 24583-24589; and Pyo et al, Targeted Gene Disruption of Matrix Metalloproteinase-9 (Gelatinase B) Suppresses Development of Experimental Abdominal Aortic Aneurysms, J. Clinical Investigation 105 (11), 1641-1649 which are all incorporated by reference in their entireties.

Method of Making

Figure 15:
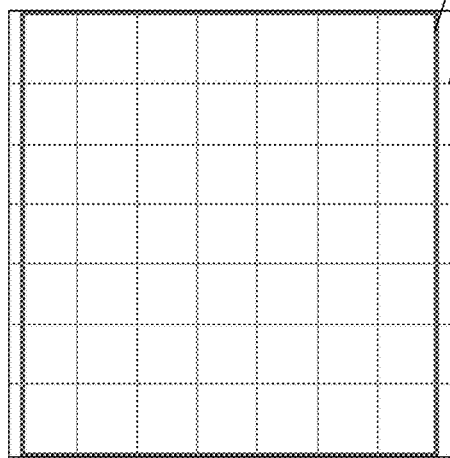
FIGS. 15 and 16 illustrate variations of the device during manufacturing.
Figure 16:
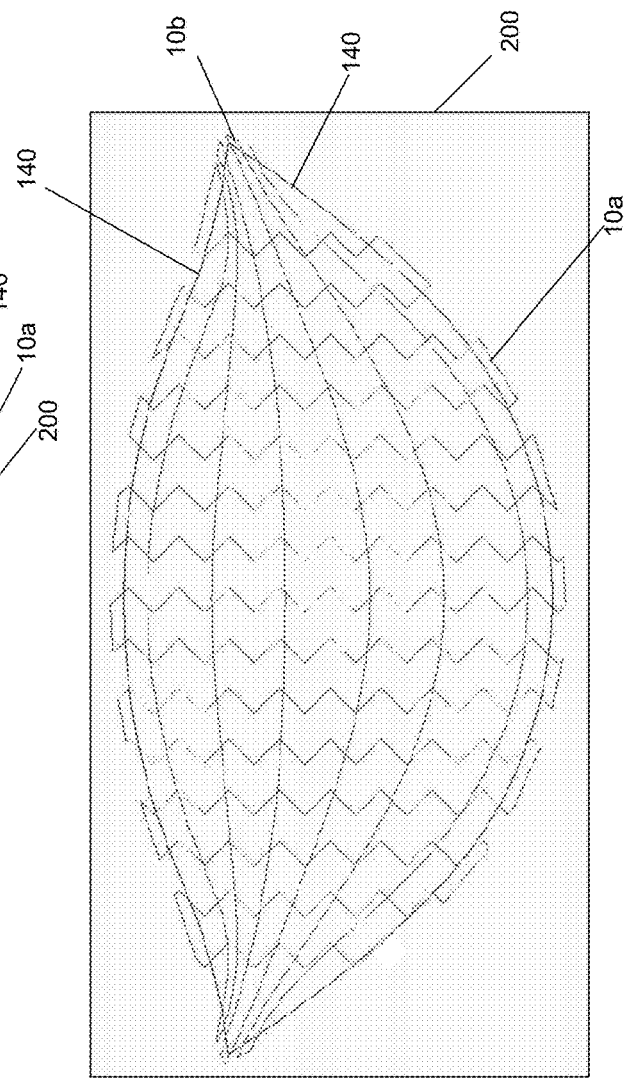

FIGS. 15 and 16 illustrate that during manufacturing of the device 140, the scaffold 200 can be stitched with the leaders 10 in desired patterns. The scaffold 200 and stitching of the leaders 10 can extend beyond the dimensions of the desired device 140. The device 140 can then be cut (e.g., die cut or laser cut) out of the scaffold 200 and stitching of leaders 10.

For example, FIG. 15 shows a variation for making the device 140 of FIG. 1 before the device 140 is cut from the scaffold 200. A die in the shape of the device 140 can cut the device 140 from the scaffold 200. Excess length of the longitudinal stitches 10a and scaffold 200 past both longitudinal ends of the device 140 can be cut away by the die.

Similarly, FIG. 16 shows a variation for making a device 140 similar to the device 140 shown in FIG. 6. Excess length of the scaffold 200 and the longitudinal and lateral leaders 10a and 10b can be cut away from all sides of the device 140.

FIGS. 17a through 17c illustrate that a first biologic matrix panel 220 can have a first edge or margin 230a. A second biological matrix panel 221 can have a second edge or margin 230b. The first biological matrix panel 220 can be bonded to the second biological matrix panel 221 along the margins 230. Bonding may comprise any of the methods described within this application.

Following the bonding, the device 140 can be in a desired three-dimensional shape and curvature, shown by the device 140 in FIGS. 14*a* through 14*c*. The degree of curvature of the cup of the device 140 can be tailored for an individual patient by varying the shape of the bonding margins. The device 140 can have complex anatomical shapes.

Two devices 140 can be made with symmetric or mirrored shapes (e.g., to be used on opposite breasts on the same patient). The device 140 can be symmetric about a central axis in any of the three orthogonal dimensions.

The panels 220 and 221 can be cut before or after the bonding to the desired shapes.

Method of Use

The device 140 can be used, for example, during breast reconstruction or augmentation surgeries. The device 140 can physically support, and provide surgical manipulation and control of an associated breast implant.

Figure 18:
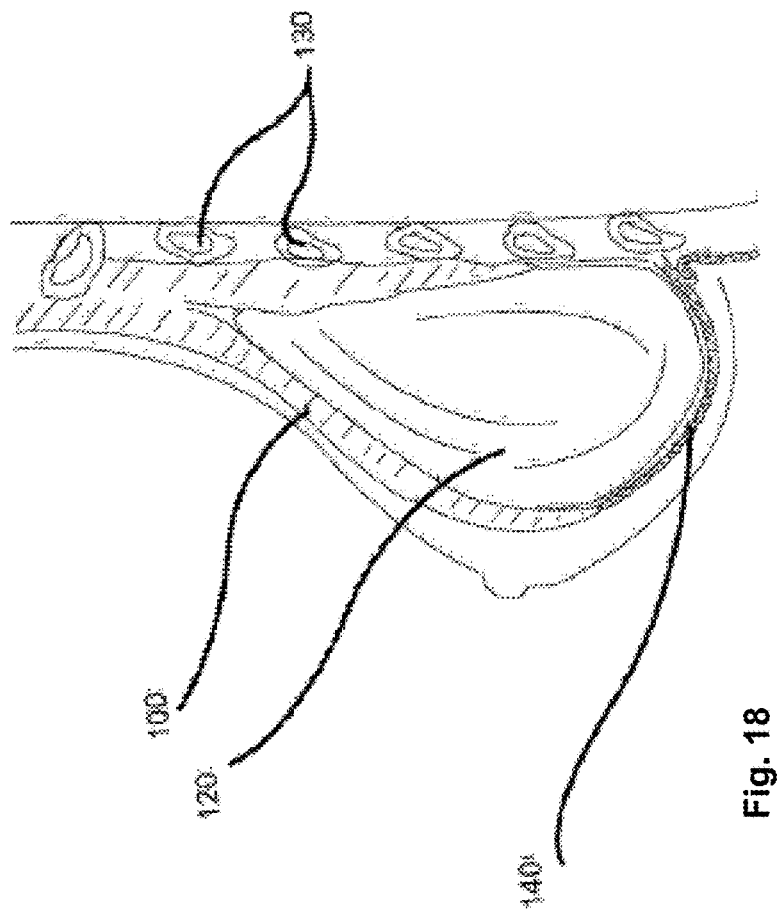
FIG. 18 illustrates a variation of a method for using the device with a breast implant in a sagittal view of a breast and surrounding tissue.

FIG. 18 illustrates that the surgical attachment device 140 can support a liquid-filled prosthetic implant 120 placed under the pectoralis major muscle 100 following a mastectomy procedure. The device 140 can take the shape of the overlying prosthetic implant 120, supporting the implant 120 and maintaining the desired contour of the breast reconstruction.

After the implant 120 is inserted into the patient, the proximal edge 16 can be inserted and attached to the chest wall. The distal edge 14 can be attached to the pectoralis major. The tips 18 can be attached to soft or hard tissue adjacent to the lateral sides of the breast implant 120. The tips 18 can be the only attachment points or attached to tissue in conjunction with the distal and/or proximal edges 14 and/or 16. Attachment of the device 140 to tissue can be via sutures, staples, brads, hooks, or combinations thereof.

Figure 19:
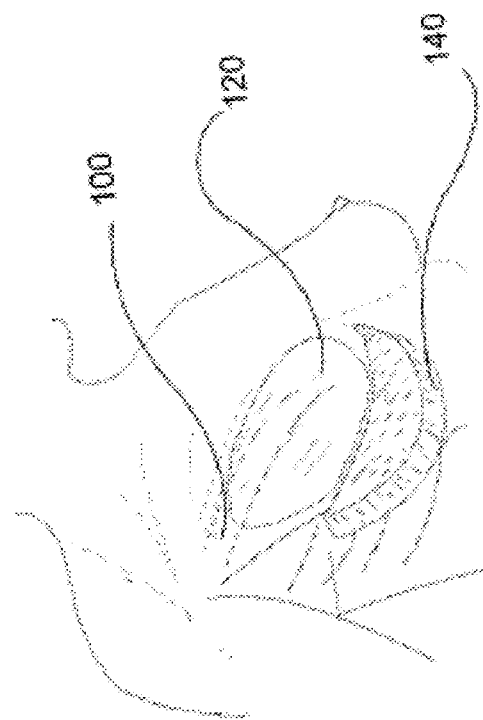
FIG. 19 illustrates a variation of a method for using the device with a breast implant in a partial see-through view of a breast and the surrounding tissue.

FIG. 19 illustrates that the lower margin of the device 140 can lend additional support and shape by the nature of a curved shape or engineered curvature, which serves to approximate and define the reconstructed inframammary fold. The engineered curvature can include curving in three-dimensions. The engineered curvature can approximate the breast implant, inframammary fold and desired appearance of the reconstructed breast. The engineered curve can eliminate creases or folds which would be present when using a flat sheet for the same purpose. By eliminating such folds and creases the breast implant takes on a more natural contour with minimal distortions.

The leaders 10 and leader patterns can impart anisotropic properties to the device 140. The device 140 can have an initial modulus of elasticity (or rate of length change relative to force applied, for example in the longitudinal direction) when initially implanted and attached to tissue. This modulus (or rate of length change relative to force applied) can be substantially identical to that of the scaffold 200. After time elapses, the scaffold 200 can stretch, for example in the longitudinal direction, due to force loads (e.g., supporting a breast implant), whereby the leaders 10 can begin to strain and deliver a resistive force through the device 140 not substantially delivered at the time of the initial implantation and attachment.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the disclosure, and variations of aspects of the disclosure can be combined and modified with each other in any combination.

We claim:

1. A method for using a surgical attachment device comprising:

forming the surgical attachment device, wherein forming comprises stitching at least a length of a first leader through a biologic sheet, wherein the first leader comprises a first synthetic material, and wherein the stitching comprises extending at least a length of the first leader from a first edge of the biological sheet across the biological sheet to a second edge of the biological sheet, and across the biological sheet to the first edge of the biological sheet;

inserting a breast implant into a patient;

attaching the surgical attachment device adjacent to the breast implant, wherein the surgical attachment device has a first post-implantation configuration and a second post-implantation configuration, wherein when the surgical attachment device is in the first post-implantation configuration, the first leader exerts a first resistive force, wherein when the surgical attachment device is in the second post-implantation configuration, the first leader exerts a second resistive force, and wherein the first resistive force is less than the second resistive force.

2. The device of claim 1, wherein the first synthetic material comprises a non-biodegradable polymer.

3. The method of claim 1, further comprising stitching a second leader through the surgical attachment device.

4. The method of claim 3, wherein the second leader comprises a second synthetic material.

5. The method of claim 4, wherein the first synthetic material has the same type of material as the second synthetic material.

6. The method of claim 3, wherein the second leader intersects the first leader.

7. The method of claim 3, wherein the second leader extends from a first edge to a second edge of the surgical attachment device.

8. The method of claim 1, wherein at least a length of the first leader has a zig-zag shape.

9. The method of claim 1, wherein at least a length of the first leader has a sinusoidal shape.

10. The method of claim 1, wherein the surgical attachment device comprises collagen.

11. The method of claim 1, wherein the surgical attachment device comprises a first layer and a second layer.

12. The method of claim 1, wherein the first leader comprises a monofilament.

13. The method of claim 1, wherein the forming further comprises cutting a shape of the surgical attachment device out of a biologic sheet.

14. The method of claim 13, wherein the cutting comprises cutting the first leader.

15. The method of claim 1, wherein the forming of the attachment device further comprises bonding a first layer to a second layer.

16. A method for using a surgical attachment device comprising:

forming the surgical attachment device, wherein forming comprises stitching at least a length of a first leader through a biologic sheet, wherein the first leader comprises a synthetic material, wherein the stitching comprises extending at least a length of the first leader from a first edge of the surgical attachment device across the surgical attachment device to a second edge of the surgical attachment device, and across the surgical attachment device to the first edge of the surgical attachment device;

inserting an implant into a target site, wherein at least part of the target site is in a breast;

inserting the surgical attachment device into the target site, wherein the surgical attachment device has a first stretched configuration and a second stretched configuration, wherein when the surgical attachment device is in the first stretched configuration, the first leader exerts a first resistive force, wherein when the surgical attachment device is in the second stretched configuration, the first leader exerts a second resistive force, and wherein the second resistive force is more than the first resistive force.

17. The method of claim 16, wherein the inserting of the implant comprises positioning the implant under the pectoralis major muscle.

18. The method of claim 16, further comprising attaching the surgical attachment device to soft and/or hard tissue adjacent to the implant.

19. A method for using an implantable support device comprising:

inserting a support device into a target site, wherein at least part of the target site is in a breast, and wherein the support device comprises at least a length of a first leader stitched through a biological sheet, wherein at least a length of the first leader extends from a first edge of the biological sheet across the biological sheet to a second edge of the biological sheet, and across the biological sheet to the first edge of the biological sheet, wherein the first leader comprises a synthetic material, and wherein the biological sheet comprises a first layer bonded to a second layer, wherein the support device has a first post-implantation configuration and a second post-implantation configuration, wherein the biological sheet is stretched more in the second post-implantation configuration than in the first post-implantation configuration, and wherein the first leader is strained more in the second post-implantation configuration than in the first post-implantation configuration.

20. The method of claim 1, further comprising removing antigenic compounds from at least part of the biological sheet.

* * * * *